(12) United States Patent
Patel et al.

(10) Patent No.: US 7,943,585 B2
(45) Date of Patent: May 17, 2011

(54) EXTENDED RELEASE ANTIBIOTIC COMPOSITION

(75) Inventors: Mahendra R. Patel, East Brunswick, NJ (US); Bhaskarbhai C. Patel, Edison, NJ (US); Amol Singh Matharu, Bedminster, NJ (US)

(73) Assignee: Sandoz, Inc., Princeton, NJ (US)

( * ) Notice: Subject to any disclaimer, the term of this patent is extended or adjusted under 35 U.S.C. 154(b) by 1461 days.

(21) Appl. No.: 10/743,367

(22) Filed: Dec. 22, 2003

(65) Prior Publication Data
US 2005/0136107 A1    Jun. 23, 2005

(51) Int. Cl.
  A01N 43/04   (2006.01)
  A61K 31/70   (2006.01)
  A61K 9/22    (2006.01)
(52) U.S. Cl. .......................................... 514/28; 424/468
(58) Field of Classification Search .................... 514/28; 424/468
  See application file for complete search history.

(56) References Cited

U.S. PATENT DOCUMENTS

| | | | |
|---|---|---|---|
| 3,034,897 A | 5/1962 | Kuhrt et al. ........................ 99/91 |
| 3,034,898 A | 5/1962 | Kuhrt et al. ........................ 99/91 |
| 3,673,106 A | 6/1972 | Jonas et al. .................... 252/356 |
| 4,083,949 A * | 4/1978 | Benedikt ........................ 424/459 |
| 4,315,041 A | 2/1982 | Fukuda et al. ................. 426/653 |
| 4,327,077 A | 4/1982 | Puglia et al. ..................... 424/38 |
| 4,389,393 A | 6/1983 | Schor et al. ..................... 424/19 |
| 4,474,768 A | 10/1984 | Bright ............................ 424/180 |
| 4,517,359 A | 5/1985 | Kobrehel et al. ............... 536/7.4 |
| 4,551,456 A * | 11/1985 | Katz ........................ 514/253.08 |
| 4,695,467 A * | 9/1987 | Uemura et al. ................ 424/502 |
| 4,808,411 A | 2/1989 | Lu et al. ......................... 424/441 |
| 4,842,866 A | 6/1989 | Horder et al. ................... 424/468 |
| 4,865,851 A | 9/1989 | James et al. .................... 424/498 |
| 5,286,489 A | 2/1994 | Tsau et al. ..................... 424/440 |
| 5,437,872 A * | 8/1995 | Lee ............................... 424/464 |
| 5,482,718 A * | 1/1996 | Shah et al. ..................... 424/480 |
| 5,609,909 A | 3/1997 | Meyer et al. ................. 427/2.14 |
| 5,707,646 A | 1/1998 | Yajima et al. ................. 424/439 |
| 5,919,489 A | 7/1999 | Saleki-Gerhardt et al. ... 424/501 |
| 5,972,373 A | 10/1999 | Yajima et al. ................. 424/439 |
| 6,010,718 A | 1/2000 | Al-Razzak et al. ........... 424/464 |
| 6,365,574 B2 | 4/2002 | Singer et al. .................... 514/29 |
| 6,399,086 B1 * | 6/2002 | Katzhendler et al. ......... 424/405 |
| 6,565,877 B1 | 5/2003 | Mukherji et al. .............. 424/441 |
| 6,632,451 B2 | 10/2003 | Penhasi et al. ................. 424/464 |
| 7,037,523 B2 * | 5/2006 | Hussain et al. ................ 424/468 |
| 2002/0012675 A1 | 1/2002 | Jain et al. ....................... 424/400 |
| 2003/0072801 A1 | 4/2003 | Curatolo et al. ............... 424/465 |
| 2003/0162730 A1 | 8/2003 | Li et al. .......................... 514/28 |
| 2003/0165563 A1 | 9/2003 | Murphy et al. ................ 424/465 |
| 2003/0190365 A1 | 10/2003 | Fergione et al. ............... 424/489 |
| 2004/0024018 A1 * | 2/2004 | Kanikanti et al. ............. 514/312 |
| 2005/0064034 A1 * | 3/2005 | Li et al. .......................... 424/469 |

FOREIGN PATENT DOCUMENTS

| | | |
|---|---|---|
| EP | 0 101 418 | 2/1984 |
| EP | 0 630 233 B1 | 12/1994 |
| JP | 49081526 | 6/1974 |
| WO | WO 93/17667 | 9/1993 |
| WO | WO 00/69415 | 11/2000 |
| WO | WO 02/17885 | 3/2002 |
| WO | WO 02/42315 | 5/2002 |
| WO | WO 03/017981 | 3/2003 |
| WO | WO 03/082248 | 10/2003 |

OTHER PUBLICATIONS

Dow Excipients, METHOCEL Products, www.dow.com.
Ethylcellulose, Handbook of Pharmaceutical Excipients, American Pharmaceutical Association, 1986, pp. 113-115.
Methlycellulose, Handbook of Pharmaceutical Excipients, American Pharmaceutical Association, 1986, pp. 181-183.

* cited by examiner

*Primary Examiner* — Paul V. Ward
*Assistant Examiner* — Sharon E Kennedy
(74) *Attorney, Agent, or Firm* — Luedeka, Neely & Graham, P.C.

(57) ABSTRACT

An extended-release antibiotic composition comprising at least one antibiotic, and greater than 50 weight percent, based on the total weight of the composition, of a polymer component, wherein said polymer component comprises at least one pharmaceutically acceptable hydrophilic polymer, and said polymer component has a viscosity of less than about 50 cps.

20 Claims, No Drawings

EXTENDED RELEASE ANTIBIOTIC COMPOSITION

FIELD OF THE INVENTION

The present invention provides an extended-release antibiotic composition comprising at least one antibiotic, and greater than 50 weight percent, based on the total weight of the composition, of a polymer component, wherein said polymer component comprises at least one pharmaceutically acceptable hydrophilic polymer, and said polymer component has a viscosity of less than about 50 centipoise (cps).

BACKGROUND OF THE INVENTION

Antibiotics, such as clarithromycin and erythromycin has been used in the treatment of common pediatric infections of the middle ear and upper respiratory tract, as well as certain forms of pneumonia that affects the elderly. Formulations containing an antibiotic are typically administered as immediate-release compositions, two or three times a day, for a regimen of 10-14 days. However, such antibiotics are extremely bitter, and even when dissolved in trace quantities in a liquid dosage form are often perceived to be unpalatable. One approach to improve the possible non-compliance with the immediate-release compositions has been to develop controlled-release solid preparations containing the antibiotic.

U.S. Pat. No. 4,842,866 describes an extended-release pharmaceutical formulation containing an active drug ingredient, sodium alginate and sodium-calcium alginate. The active drug ingredient is present in an amount up to 70% by weight of the formulation.

U.S. Pat. No. 4,808,411 describes a taste-masked composition in the form of granules which contain 25% to 90% of erythromycin or a derivative thereof, and 5% to 75% of an acrylic acid polymer.

U.S. Pat. No. 4,389,393 describes a sustained-release therapeutic composition containing an active agent and from 5 wt. % to about 30 wt. % of hydroxypropylmethyl cellulose or a mixture of hydroxypropylmethyl celluloses.

International Application WO 03/017981 describes controlled-release formulations containing a drug having a water solubility of less than 1 part per 30 parts water, and from about 0.1% $^w/_w$ to about 4.5% $^w/_w$ of a rate-controlling, high-viscosity cellulosic ether polymer.

International Application WO 02/017885 describes a controlled-release pharmaceutical composition containing erythromycin A or a derivative thereof and from about 0.1% $^w/_w$ to about 4% $^w/_w$ of a rate-controlling polymer. Examples of rate-controlling polymers are a carbohydrate gum, polyuronic acid salt, cellulose ether and acrylic acid polymer.

U.S. Pat. No. 5,286,489 describes a porous drug-polymer matrix formed by admixing one or more bitter tasting active ingredient and a methyl methacrylic ester copolymer in at least a 1:1 by weight ratio of active ingredient to copolymer. U.S. Pat. No. 5,286,489 states that an effective taste making amount of the copolymer is used.

U.S. Pat. No. 6,565,877 describes a taste-masked composition containing a bitter tasting drug, such as clarithromycin, and a combination of two enteric polymers comprising a methacrylic acid co-polymer and a phthalate polymer. U.S. Pat. No. 6,565,877 states that for optimal taste masking effect, total polymer to drug ratio is at least 1:4.

U.S. Pat. No. 6,010,718 describes an extended-release composition containing an erythromycin derivative and from about 5% to about 50% by weight of a pharmaceutically acceptable polymer.

SUMMARY OF THE INVENTION

The invention provides an extended-release antibiotic composition comprising at least one antibiotic, and greater than 50 weight percent, based on the total weight of the composition, of a polymer component, wherein said polymer component comprises at least one pharmaceutically acceptable hydrophilic polymer, and said polymer component has a viscosity of less than about 50 cps.

According to another aspect, the invention provides a process for preparing an extended-release antibiotic composition, said process comprising blending at least one antibiotic, a polymer component, and optionally one or more excipients to form a composition, wherein the polymer component is present in an amount of greater than 50 weight percent, based on the total weight of the composition, wherein said polymer component comprises at least one pharmaceutically acceptable hydrophilic polymer, and said polymer component has a viscosity of less than about 50 cps.

According to another aspect, the invention provides a method of using an extended-release antibiotic composition comprising of at least one antibiotic and greater than 50 weight percent, based on the total weight of the composition, of a polymer component, wherein said polymer component comprises at least one pharmaceutically acceptable hydrophilic polymer, and said polymer component has a viscosity of less than about 50 cps, wherein said method comprises administering the composition in an effective amount for the treatment of bacterial infection in a patient in need of such treatment.

The present inventors have determined that an antibiotic composition comprising a polymer component in an amount greater than 50 wt. %, based on the total weight of the composition, reduces the plasma level variability of the antibiotic over an extended period of time as compared to antibiotic compositions containing less than 50 wt. % of a polymer component.

DETAILED DESCRIPTION OF THE INVENTION

The invention provides an extended-release antibiotic composition comprising at least one antibiotic, and greater than 50 weight percent, based on the total weight of the composition, of a polymer component, wherein said polymer component comprises at least one pharmaceutically acceptable hydrophilic polymer, and said polymer component has a viscosity of less than about 50 cps. As used herein, "extended-release" means the antibiotic is not immediately released from the composition, and includes controlled-release, sustained-release, pulsatile-release and delayed-release.

Preferred antibiotics include erythromycin; azithromycin, clarithromycin; fluoroquinolones, such as ciprofloxacin and norfloxacin; cephalosporins, such as cefuroxime and ceftriaxone; and tetracyclic antibiotics, e.g., chloramphenicol and chlorpromazine. As used herein, "antibiotic" includes salts and derivatives thereof. A combination of antibiotics may also be used. Preferably, the antibiotic is clarithromycin.

The antibiotic is present in an amount of from about 1 wt. % to about 50 wt. %, based on the total weight of the composition. Preferably, the antibiotic is present in an amount of from about 10 wt. % to about 45 wt. %, more preferably about 30 wt. % to about 43 wt. %, based on the total weight of the composition. Typically, the amount of antibiotic in the compositions of the invention varies from 100 to 1500 mg, preferably about 500 mg.

The pharmaceutically acceptable polymer component comprises at least one hydrophilic polymer. As used herein, "pharmaceutically acceptable" means polymers which are within the scope of sound medical judgment, suitable for use in contact with the tissues of humans without undue toxicity, irritation and allergic response, in keeping with a reasonable benefit/risk ratio. As used herein, "polymer" includes copolymers, terpolymers, etc. Preferred pharmaceutically acceptable hydrophilic polymers for use in the antibiotic compositions of the invention are water soluble and include hydroxypropylmethyl cellulose, hydroxypropyl cellulose, hydroxyethyl cellulose, methyl cellulose, carboxymethylethyl cellulose, sodium carboxymethyl cellulose, carboxymethyl cellulose, carboxyethyl cellulose, polyvinylalcohol, sodium alginate, polyvinylpyrrolidone, vinyl acetate/crotonic acid copolymers, methacrylic acid copolymers, methyl methacrylic ester copolymers, maleic anhydride/methyl vinyl ether copolymers and poly(ethylene oxide). More preferably, the polymer is selected from hydroxypropylmethyl cellulose, hydroxypropyl cellulose, and poly(ethylene oxide). Most preferably, the polymer is hydroxypropylmethyl cellulose. The polymer component may include one polymer or a combination of polymers.

Hydroxypropylmethyl cellulose is a polymer which is available in many forms, including forms of different molecular weight, extremely different viscosity and different substitution grade. It is within the scope of the invention to use mixtures or blends of two or more different forms of hydroxypropylmethyl cellulose as the polymer component. In one preferred embodiment, the polymer component comprises a mixture of hydroxypropylmethyl celluloses having different viscosities. For example, two grades of hydroxypropylmethyl cellulose polymers which are especially preferred in combination for use in the antibiotic compositions of the invention are Methocel E5 LV Premium, which has a viscosity of 5 cps, and Methocel E15 LV Premium, which has a viscosity of 15 cps. Methocel E5 LV Premium and Methocel E15 LV Premium are commercially-available from Dow Chemical. Mixtures of different viscosity grades of the same polymer shall be considered to comprise a single polymer for purposes of the invention.

It is within the scope of the invention, for example in the case of tablets, to use one or more pharmaceutically acceptable hydrophilic polymer in the tablet core and one or more pharmaceutically acceptable hydrophilic polymer in the tablet coating.

The polymer component is present in an amount of greater than 50 wt. %, based on the total weight of the composition. Preferably, the polymer component is present in an amount of from about 51 wt. % to about 75 wt. %. More preferably, the polymer component is present in an amount of from about 53 wt. % to about 70 wt. %, most preferably from about 55 wt. % to about 60 wt. %.

The polymer component has a viscosity of less than about 50 centipoise (cps), as determined using a Ubbelohde viscometer, 2% by weight of polymer in water, at a temperature of 20° C.+/−0.1° C., according to the American Society for Testing and Materials (ASTM, D-445). More preferably, the polymer component has a viscosity of about 1 cps to about 30 cps, most preferably, from about 5 cps to about 20 cps. It is within the scope of the invention for the polymer component to include at least one pharmaceutically acceptable hydrophilic polymer having a viscosity of greater than 50 cps provided that such polymer is combined with at least one pharmaceutically acceptable hydrophilic polymer having a viscosity of less than 50 cps to yield a combination of polymers having a viscosity of from about 1 cps to about 50 cps.

In addition to the antibiotic and polymer component, the antibiotic compositions may contain one or more excipients. Examples of such excipients are glidants, binders, fillers, diluents, anti-caking agents, amino acids, fillers, solubilizers, disintegrants, lubricants, emulsifiers, stabilizers, anti-oxidants, anti-adherents, preservatives, electrolytes, glidants, wetting agents, surface active agents, colors and pigments, flavoring agents, sweeteners, adsorbents, taste-masking agents and enteric coatings. A combination of excipients may also be used. Preferably, the excipients meet the standards of the National Formulary (NF) or United States Pharmacopoeia (USP). The extended-release characteristics for the release of the antibiotic from the compositions of the invention may be varied by changing the type or amount of polymer component and/or the type or amount of excipients which may be present.

Examples of glidants include, but are not limited to, silica, magnesium trisilicate, powdered cellulose, starch, talc and tribasic calcium phosphate. A preferred glidant is silicon dioxide.

Fillers or diluents are typically added to a small amount of the active drug to increase the size of the tablet. Examples of fillers or diluents include, but are not limited to, spray-dried or anhydrous lactose; sucrose; dextrose; starch; pre-gelatinized starch; polyols, such as mannitol, sorbitol and xylitol; cellulose, such as microcrystalline cellulose; and inorganic salts, such as dibasic calcium phosphate, tribasic calcium phosphate and calcium sulfate. Preferably, the filler or diluent is lactose monohydrate.

Disintegrants are included in tablet formulations to break the tablets into particles of the active pharmaceutical ingredient and excipients which will facilitate dissolution of the active ingredient and enhance bioavailability of the active ingredient. Examples of disintegrants include, but are not limited to, starch and starch derivatives, including cross-linked sodium salt of a carboxymethyl ether of starch, such as sodium starch glycolate; pre-gelatinized starch, such as Starch 1500; sodium starch glycolate; cross-linked sodium carboxymethyl cellulose, such as croscarmellose sodium; cross-linked polyvinylpyrrolidone, such as crospovidone; and microcrystalline cellulose. A preferred disintegrant is cross-linked sodium carboxymethyl cellulose.

Binders are used as a wet granulation excipient to agglomerate the active pharmaceutical ingredient and the other excipients. A binder is selected to improve powder flow and to improve compactibility. Examples of binders include, but are not limited to, cellulose derivatives, such as microcrystalline cellulose, methylcellulose, carboxymethycellulose sodium, hydroxypropyl methylcellulose, hydroxyethyl cellulose and hydroxypropyl cellulose; polyvidone; polyvinyl pyrrolidone; gelatin; natural gums, such as acacia, tragacanth, guar and pectin; starch paste; pre-gelatinized starch; sucrose; corn syrup; polyethylene glycols and sodium alginate; ammonium calcium alginate; magnesium aluminum silicate; and polyethylene glycols. A preferred binder is pre-gelatinized starch.

Several co-processed filler-binders are commercially-available, including cellactose (α-lactose monohydrate and powdered cellulose 75:25), microcelac (α-lactose monohydrate and powdered cellulose 75:25), ludipress (93% β-lactose monohydrate, 3.5% polyvinylpyrrolidone and 3.5% crospovidone) and pharmatose DCL 40 (95%-lactose and 5% lactitol).

Lubricants are used in tablet formulation to prevent sticking of the tablet to the punch faces and to reduce friction during the compression stages. Examples of lubricants include, but are not limited to, vegetable oils, such as hydrogenated vegetable oil or hydrogenated castor oil; polyethylene glycols, such as PEG-4000 and PEG-6000; stearic acid; salts of stearic acid, such as magnesium stearate, sodium stearate and sodium stearyl fumarate; mineral salts, such as talc; inorganic salts; organic salts, such as sodium benzoate, sodium acetate and sodium oleate; and polyvinyl alcohols. A preferred lubricant is magnesium stearate.

The antibiotic compositions of the invention are prepared in a solid dosage form suitable for oral administration. Solid dosage forms include capsules, caplets, powders and tablets. In one embodiment, the compositions are compressed into a tablet. Tablets may include sugar-coated tablets, film-coated tablets, enteric-coated tablets, multiple-compressed tablets, bi-layer tablets and effervescent tablets. The tablet formulation can be prepared by wet granulation, dry granulation, direct compression or by any other technique known in the pharmaceutical art. In another embodiment, the compositions are enclosed in a capsule, preferably a hard gelatin capsule.

The following non-limiting examples illustrate further aspects of the invention.

Example 1

Preparation of Clarithromycin Tablets Containing 56.8 wt. % Polymer

| Ingredient | Amount per Tablet |
|---|---|
| Tablet Core | |
| Clarithromycin | 500 mg |
| Methocel E5LV Premium | 470 mg |
| Methocel E15LV Premium | 200 mg |
| Magnesium Stearate | 15 mg |
| Silicone Dioxide NF (Syloid-244) | 5 mg |
| Coating | |
| Methocel E5 LV Premium | 14 mg |
| Methocel E15 LV Premium | 6 mg |
| Titanium Dioxide USP | 2 mg |
| Polyethylene Glycol 3350 NF | 2 mg |
| Purified Water | q.s. |

The clarithromycin, Methocel E5 LV, Methocel E15 LV, silicone dioxide and 5 mg of magnesium stearate were mixed in a 800 L high-shear mixer with an impeller set at 350 rpm and chopper set at 2000 rpm to form a blend. The blend was compacted using a roller compacter. The compacted material was milled using a Flak Crusher equipped with 2.0 mm wire-mesh screen. To the milled blend, 10 mg of magnesium stearate was added and mixed in a V-blender. This blend was compressed into a tablet and the tablets were coated.

Example 2

Preparation of Clarithromycin Tablets Containing 60 wt. % Polymer

| Ingredient | Amount per Tablet |
|---|---|
| Tablet Core | |
| Clarithromycin | 500 mg |
| Methocel K 100LV | 130 mg |
| Magnesium Stearate | 6.5 mg |
| Lactose | 13.5 mg |
| Purified Water | q.s. |
| Coating | |
| Eudragit L100-55 | 650 mg |

Clarithromycin, Methocel and lactose were mixed to form a powder mixture. Water was added gradually to obtain a uniform granulation. The granulation was dried in an oven at 60° C. for about 45 minutes. The dried granules were passed through a hand screen #16. Magnesium stearate was added to the screened blend and mixed. The final blend was compressed into tablets and coated.

Example 3

Preparation of Clarithromycin Tablets Containing 54.3 wt. % Polymer

| Ingredient | Amount per Tablet |
|---|---|
| Tablet Core | |
| Clarithromycin | 500 mg |
| Methocel K 100LV | 130 mg |
| Magnesium Stearate | 6.5 mg |
| Lactose | 13.5 mg |
| Purified Water | q.s. |
| Coating | |
| Pharmacoat 603 | 540 mg |
| Sodium Bicarbonate | 20 mg |
| Fumaric Acid | 20 mg |
| Magnesium Stearate | 5 mg |

The tablets were prepared according to the procedure set forth in Example 2.

Example 4

Preparation of Clarithromycin Bi-Layer Tablets Containing 56.3 wt. % Polymer

| Ingredient | Amount per Tablet |
|---|---|
| Tablet Layer 1 | |
| Clarithromycin | 500 mg |
| Methocel K 100LV | 130 mg |
| Magnesium Stearate | 6.5 mg |
| Lactose | 13.5 mg |
| Water | q.s. |
| Tablet Layer 2 | |
| Clarithromycin | 50 mg |
| Pharmacoat 603 | 545 mg |
| Povidone K30 | 15 mg |
| Purified Water | q.s. |
| Magnesium Stearate | 5 mg |

Tablet Layer 1 and Tablet Layer 2 were individually prepared. With regard to Tablet Layer 1, clarithromycin, Methocel K 100LV and lactose were mixed to form a powder mixture. Water was added gradually to obtain a uniform granulation. The granulation was dried in an oven at 60° C. for about 45 minutes. The dried granules were passed through a hand screen #16. Magnesium stearate was added to the screened blend and mixed. With regard to Tablet Layer 2, clarithromycin, Pharmacoat and Povidohe were mixed to form a powder mixture. Water was added gradually to obtain a uniform granulation. The granulation was dried in an oven at 60° C. for about 45 minutes. The dried granules were passed through a hand screen #16. Magnesium stearate was added to the screened blend and mixed.

The final blends of Tablet Layer 1 and Tablet Layer 2 were compressed using a bi-layer tableting machine to form bi-layer tablets.

Example 5

Preparation of Clarithromycin Bilayer Tablets Containing 55.1 wt. % Polymer

| Ingredient | Amount per Tablet |
| --- | --- |
| Tablet Layer 1 | |
| Clarithromycin | 475 mg |
| Methocel K 100LV | 102 mg |
| Magnesium Stearate | 6 mg |
| Lactose | 17 mg |
| Tablet Layer 2 | |
| Clarithromycin | 25 mg |
| Pharmacoat 603 | 545 mg |
| Purified Water | q.s. |
| Magnesium Stearate | 5 mg |

The bi-layer tablets were prepared according to the procedure set forth in Example 4. The dissolution of the bi-layer tablets was evaluated and the results are summarized in Table I.

TABLE I

Tablets 500 mg, USP App. II (paddle), 50 rpm, Acetate Buffer pH = 5.0

| Time (hrs) | Ex. 5 (% avg. dissolved clarithromycin) |
| --- | --- |
| 0.5 | 2.5 |
| 1 | 4.4 |
| 2 | 7.2 |
| 3 | 11.4 |
| 4 | 17.4 |
| 5 | 23.1 |
| 6 | 29 |
| 7 | 35.2 |
| 8 | 41.2 |
| 9 | 45.9 |
| 10 | 50.9 |
| 11 | 55.1 |
| 12 | 58.1 |

The results in Table I illustrate the extended release characteristics of the tablets prepared according to the invention. Even after 12 hours, 41.9% of the clarithromycin remains in the tablets.

Example 6

Preparation of Clarithromycin Tablets Containing 50.2 wt. % Polymer

| Ingredient | Amount per Tablet |
| --- | --- |
| Clarithromycin | 500 mg |
| Methocel K 100LV | 520 mg |
| Magnesium Stearate | 15 mg |

Clarithromycin and Methocel K 100 LV mixed with a stainless steel spatula to form a powder mixture. Magnesium stearate was added to the powder mixture and mixed. The mixture was compressed into tablets.

Example 7

Preparation of Clarithromycin Tablets Containing 55.2 wt. % Polymer

| Ingredient | Amount per Tablet |
| --- | --- |
| Clarithromycin | 500 mg |
| Pharmacoat 606 | 640 mg |
| Magnesium Stearate | 20 mg |

Clarithromycin, Pharmacoat 606 and magnesium stearate were mixed to form a powder mixture. Slugs were made using a Carver Press at 15 tons of pressure. The slugs were milled using a Fitz-mill equipped with 0.093" screen at 2450 rpm. The resulting agglomerated powder was compressed into tablets.

The dissolution of the tablets was evaluated and the results are summarized in Table II.

TABLE II

Tablets 500 mg, USP App. II (paddle), 50 rpm, 900 mL 0.01 N HCl for 2 Hours, then Phosphate Buffer pH = 6.8

| Time (hrs) | Ex. 7 (% avg. dissolved clarithromycin) |
| --- | --- |
| 0.5 | 3.7 |
| 1 | 6.3 |
| 2 | 10.6 |
| 3 | 20.5 |
| 4 | 29.1 |
| 5 | 35.6 |
| 6 | 41.9 |
| 7 | 46.9 |
| 8 | 50.9 |
| 9 | 53.1 |
| 10 | 55.4 |
| 11 | 55.8 |
| 12 | 56.1 |

The results in Table II illustrate the extended release characteristics of the tablets prepared according to the invention. Even after 12 hours, 43.9% of the clarithromycin remains in the tablets.

Example 8

Preparation of Clarithromycin Tablets Containing 55.2 wt. % Polymer

| Ingredient | Amount per Tablet |
|---|---|
| Clarithromycin | 500 mg |
| Polyox NSRN-105 | 640 mg |
| Magnesium Stearate | 20 mg |

Tablets were prepared according to the procedure set forth in Example 7, except that Pharmacoat 606 was replaced with Polyox.

Example 9

Preparation of Clarithromycin Tablets Containing 53.2 wt. % Polymer

| Ingredient | Amount per Tablet |
|---|---|
| Clarithromycin | 500 mg |
| Methocel E5 LV Premium | 295 mg |
| Methocel E15 LV Premium | 295 mg |
| Magnesium Stearate | 20 mg |
| Purified Water | q.s. |

Clarithromycin, Methocel E5 LV and Methocel E15 LV were mixed. Water (18 g) was gradually added to the mixture and mixing was continued until a uniform granulation was obtained. The granulation was dried in an oven at 60° C. for about 45 minutes. The dried granules were passed through a hand screen #16. Magnesium stearate was added to the screened blend and mixed for about 1 minute. The final blend was compressed into tablets.

Example 10

Preparation of Clarithromycin Tablets Containing 58.1 wt. % Polymer

| Ingredient | Amount per Tablet |
|---|---|
| Tablet Core | |
| Clarithromycin | 500 mg |
| Methocel E5 LV Premium | 469 mg |
| Methocel E15 LV Premium | 201 mg |
| Magnesium Stearate | 20 mg |
| Coating | |
| HPMC E3 | 50 mg |

Clarithromycin and 25 mg of Methocel E5 LV were mixed. Water (20 g) was gradually added to the mixture and mixing was continued until a uniform granulation was obtained. The granulation was dried in an oven at 60° C. for about 45 minutes. The dried granules were passed through a hand screen #16. The remaining amount of Methocel E5 LV and Methocel E15 LV were mixed with the screened blend. Magnesium stearate was added to the blend and mixed. The final blend was compressed into tablets and coated.

Example 11

Preparation of Clarithromycin Tablets Containing 56.8 wt. % Polymer

| Ingredient | Amount per Tablet |
|---|---|
| Clarithromycin | 500 mg |
| Methocel E5 LV Premium | 670 mg |
| Magnesium Stearate | 10 mg |

Clarithromycin and 25 mg of Methocel E5 LV were mixed. Water (20 g) was gradually added to the mixture and mixing was continued until a uniform granulation was obtained. The granulation was dried in an oven at 60° C. for about 45 minutes. The dried granules were passed through a hand screen #16. The remaining amount of Methocel E5 LV was mixed with the screened blend. Magnesium stearate was added to the blend and mixed. The final blend was compressed into tablets.

The dissolution of the tablets was evaluated and the results are summarized in Table III.

TABLE III

Tablets 500 mg, USP App. II (paddle with sinker), 50 rpm, 900 mL 0.01 N HCl for 2 Hours, then Phosphate Buffer pH = 6.8

| Time (hrs.) | Ex. 11 (% avg. dissolved clarithromycin) |
|---|---|
| 0.5 | 3.3 |
| 1 | 5.4 |
| 2 | 8.4 |
| 4 | 12.7 |
| 6 | 17 |
| 8 | 20.8 |
| 10 | 24.1 |
| 12 | 26.8 |

The results in Table III illustrate the extended release characteristics of the tablets prepared according to the invention. Even after 12 hours, 73.2% of the clarithromycin remains in the tablets.

Example 12

Preparation of Clarithromycin Tablets Containing 56.8 wt. % Polymer

| Ingredient | Amount per Tablet |
|---|---|
| Clarithromycin | 500 mg |
| Methocel E5 LV Premium | 10 mg |
| Purified Water | q.s. |
| Methocel E5 LV Premium | 459 mg |

| Ingredient | Amount per Tablet |
| --- | --- |
| Methocel E15 LV Premium | 201 mg |
| Magnesium Stearate | 10 mg |

Clarithromycin and 25 mg of Methocel E5 LV were mixed. Water (20 g) was gradually added to the mixture and mixing was continued until a uniform granulation was obtained. The granulation was dried in an oven at 60° C. for about 45 minutes. The dried granules were passed through a hand screen #16. The remaining amount of Methocel E5 LV and Methocel E15 LV were mixed with the screened blend. Magnesium stearate was added to the blend and mixed. The final blend was compressed into tablets.

While the invention has been described with particular reference to certain embodiments thereof, it will be understood that changes and modifications may be made by those of ordinary skill within the scope and spirit of the following claims:

What is claimed is:

1. An extended-release antibiotic composition comprising at least one antibiotic, and greater than 50 weight percent, based on the total weight of the composition, of a polymer component, wherein said polymer component comprises at least one pharmaceutically acceptable hydrophilic and water-soluble polymer, and said polymer component has a viscosity of less than about 50 cps, wherein the at least one hydrophilic and water-soluble polymer is present in an amount greater than 10 weight percent of the composition.

2. The composition according to claim 1, wherein the polymer is selected from the group consisting of hydroxypropylmethyl cellulose, hydroxypropyl cellulose, hydroxyethyl cellulose, methyl cellulose, carboxymethylethyl cellulose, sodium carboxymethyl cellulose, ethylcarboxyethyl cellulose, polyvinylalcohol, sodium alginate, polyvinylpyrrolidone, vinyl acetate/crotonic acid copolymers, methacrylic acid copolymers, methyl methacrylic ester copolymers, maleic anhydride/methyl vinyl ether copolymers, poly(ethylene oxide), and combinations thereof.

3. The composition according to claim 2, wherein the polymer is selected from the group consisting of hydroxypropylmethyl cellulose, hydroxypropyl cellulose and poly(ethylene oxide).

4. The composition according to claim 3, wherein the polymer is hydroxypropylmethyl cellulose.

5. The composition according to claim 1, wherein the antibiotic is selected from the group consisting of erythromycin, azithromycin, clarithromycin, fluoroquinolones, cephalosporins, tetracyclic antibiotics and combinations thereof, including salts and derivatives thereof.

6. The composition according to claim 5, wherein the antibiotic is clarithromycin.

7. The composition according to claim 1, wherein the antibiotic is present in an amount of from about 1 wt. % to about 50 wt. %, based on the total weight of the composition.

8. The composition according to claim 7, wherein the antibiotic is present in an amount of from about 10 wt. % to about 45 wt. %.

9. The composition according to claim 8, wherein the antibiotic is present in an amount of from about 30 wt. % to about 43 wt. %.

10. The composition according to claim 1, wherein the polymer is present in an amount of from about 51 wt. % to about 75 wt. %, based on the total weight of the composition.

11. The composition according to claim 10, wherein the polymer is present in an amount of from about 53 wt. % to about 70 wt. %.

12. The composition according to claim 11, wherein the polymer is present in an amount of from about 55 wt. % to about 60 wt. %.

13. The composition according to claim 1, wherein the polymer has a viscosity of about 1 cps to about 30 cps.

14. The composition according to claim 13, wherein the polymer has a viscosity of about 5 cps to about 20 cps.

15. A process for preparing an extended-release antibiotic composition according to claim 1, said process comprising blending at least one antibiotic, a polymer component, and optionally one or more excipients to form a composition, wherein the polymer component is present in an amount of greater than 50 weight percent, based on the total weight of the composition, wherein said polymer component comprises at least one pharmaceutically acceptable hydrophilic and water-soluble polymer, and said polymer component has a viscosity of less than about 50 cps, wherein the at least one hydrophilic and water-soluble polymer is present in an amount greater than 10 weight percent of the composition.

16. The process according to claim 15, wherein the antibiotic is clarithromycin.

17. The process according to claim 15, wherein the excipient is selected from the group consisting of a binder, diluent, anti-caking agent, amino acid, filler, solubilizer, disintegrant, lubricant, emulsifier, flavorant, solvent, stabilizer, anti-oxidant, anti-adherent, preservative, electrolyte, glidant, coating and combinations thereof.

18. The composition according to claim 1, which is in a form selected from the group consisting of a capsule, caplet, powder and tablet.

19. The composition according to claim 18, which is in the form of a tablet.

20. A method of using an extended-release antibiotic composition according to claim 1, comprising at least one antibiotic, and greater than 50 weight percent, based on the total weight of the composition, of a polymer component, wherein said polymer component comprises at least one pharmaceutically acceptable hydrophilic and water-soluble polymer, and said polymer component has a viscosity of less than about 50 cps, wherein the at least one hydrophilic and water-soluble polymer is present in an amount greater than 10 weight percent of the composition, wherein said method comprises administering the composition in an effective amount for the treatment of bacterial infection in a patient in need of such treatment.

* * * * *